United States Patent [19]

Staubli et al.

[11] Patent Number: 5,169,309
[45] Date of Patent: Dec. 8, 1992

[54] ABUTMENT FOR DENTAL APPLIANCES AND THE LIKE

[75] Inventors: Peter E. Staubli, San Carlos; Greg P. Siekierski, Redwood City, both of Calif.

[73] Assignee: Attachments International, Inc., San Mateo, Calif.

[21] Appl. No.: 625,306

[22] Filed: Dec. 10, 1990

Related U.S. Application Data

[63] Continuation-in-part of Ser. No. 464,160, Jan. 12, 1990, abandoned.

[51] Int. Cl.⁵ .............................................. A61C 8/00
[52] U.S. Cl. .................................... 433/174; 433/173
[58] Field of Search ........................ 433/172, 174, 173

[56] References Cited

U.S. PATENT DOCUMENTS

| | | | |
|---|---|---|---|
| 3,656,236 | 4/1972 | Kurer | 433/174 |
| 3,905,109 | 9/1975 | Cohen et al. | 433/174 |
| 4,016,651 | 4/1977 | Kawahara et al. | 433/172 |
| 4,872,839 | 10/1989 | Brajnovic | 433/173 |

*Primary Examiner*—John J. Wilson
*Assistant Examiner*—Cindy A. Cherichetti
*Attorney, Agent, or Firm*—John A. Bucher

[57] ABSTRACT

An abutment and method of its use are disclosed for securing dental appliances of other physiological appliances having a wide variety of confugurations to an implant mounted in a bony substrate, the abutment including an indexing element means forming an abutment surface surrounding the indexing element and separate threaded attachment for the appliance, either integrally with the implant or on an abutment attachable to the implant, the indexing element being formed with a cylindrical taper extending outwardly from the abutment surface and one or more, preferably six, planar facets intersecting the tapered surface adjacent the abutment surface but with portions of the tapered surface intermediate the facets extending substantially toward the abutment surface. The tapered surface is preferably in the range of about ten to thirty degrees, more preferably about thirteen to seventeen degrees, relative to an axis of the indexing element, the overall axial length of the indexing element preferably being at least about 0.020 inches, more preferably in the range of about 0.030–0.100 inches.

25 Claims, 2 Drawing Sheets

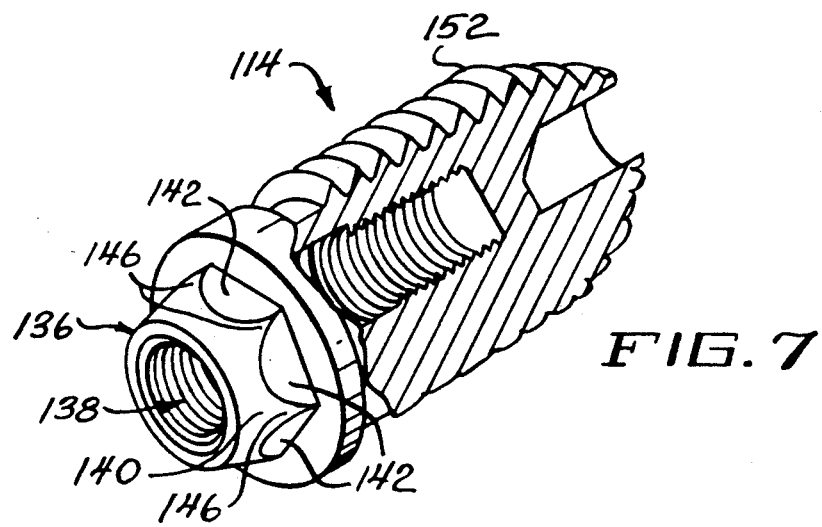
FIG. 7
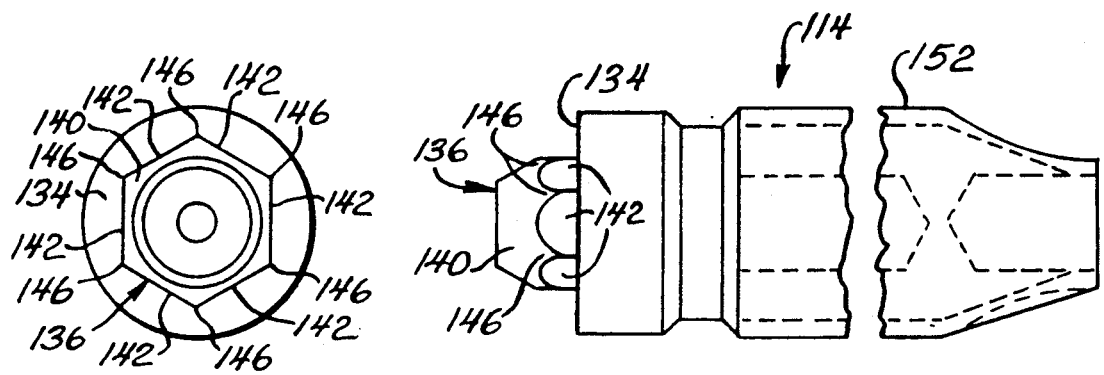
FIG. 9    FIG. 8
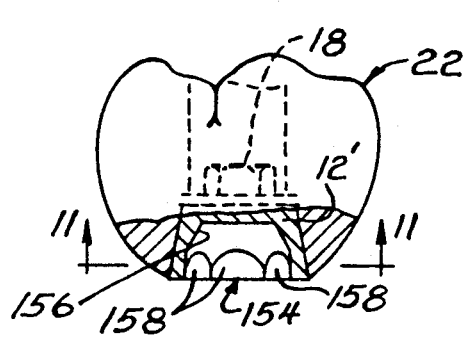    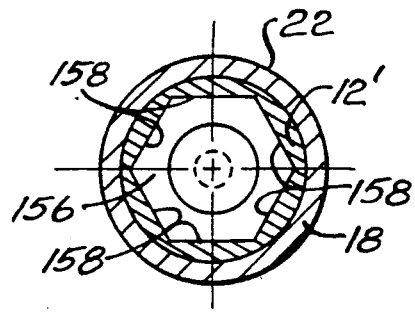
FIG. 10    FIG. 11

ABUTMENT FOR DENTAL APPLIANCES AND THE LIKE

This is a continuation-in-part of application Ser. No. 07/464,160 filed Jan. 12, 1990 by Peter E. Staubli, et al., the same inventors as for the present invention, that application now being abandoned.

FIELD OF THE INVENTION

The present invention relates to a mounting insert (or universal modification abutment) and method of its use for securing physiological appliances to implants in a bony substrate and more particularly to such a mounting and method of use for securing dental appliances to such an implant.

BACKGROUND OF THE INVENTION

In a variety of physiological applications, particularly dentistry, appliances are provided as fixed detachable components on the human body, usually mounted by means of one or more implants which are attached to a bony substrate. For dental applications, these appliances are typically in the form of fixed artificial teeth, bridges, dentures and the like which are preferably detachable or removable. However, it is to be understood that such appliances may be constructed with a variety of configurations including telescopic units and misalignment appliances for use with misangled teeth for example as well as overlay dentures including bars attached to artificial teeth or a combination of artificial and natural teeth.

Variations in appliances as summarized above are well known to those skilled in the art and, accordingly, no further discussion of all of the various configurations is believed necessary. In any event, it is to be understood that the features of the present invention apply to all such variations of such appliances.

More broadly, such appliances may also take a variety of forms, referred to herein by the term "physiological", such as other physical features of the human body, particularly in connection with maxiofacial restoration where eyes, ears, noses, cheeks, etc. are removably attached to underlying bony substrates or structures.

In attaching such appliances to the underlying substrate, an implant is first mounted within the substrate. For example, the implant may be threaded into place in the substrate or secured therein by press-fit engagement or simple placement or a combination of the above.

Once the implant is secured in place within the substrate, it provides a mounting platform for a variety of appliances as summarized above. Generally, the appliance includes an abutment device suitable for attachment to the implant for example by threaded engagement, press-fit engagement, cementing or a combination thereof.

In typical processes, particularly for dental applications, a plastic component is commonly employed initially to form a mold cavity prior to casting of the actual appliance. Such processes are well known to those skilled in the art and are not described in further detail herein. In any event, where the component is made from plastic, elastomer or other material and used to form a tooth or teeth, the component is then commonly "burned out" and replaced by a metal frame forming part of the actual or finished appliance during the casting process.

Accordingly, the term "appliance" is employed herein to refer both to finished appliances as well as to initial devices such as the plastic component described above for use in casting of the finished appliance. As is also well known to those skilled in the art, the plastic component may also be termed a waxing sleeve, sleeve, coping, cylinder, etc.

In securing the applicant to the implant, directly or indirectly, it is necessary to resist substantial forces acting in a variety of directions including axially and laterally as well as angularly or in rotation. Accordingly, it has been found necessary in the past to stabilize the mounting of the appliance (directly or indirectly) upon the implant against one or more of these types of forces.

Generally, for dentures and other similar appliances commonly provided with multiple anchor points or implants, it is most important to provide stability against axial and lateral forces. For artificial teeth and the like including a single anchor point or implant, it is particularly important to provide stability against angular or rotational forces acting upon the appliance.

Generally, the prior art has employed cylindrically tapered indexing elements for securing dentures and the like to multiple implants. Such tapered indexing elements have been found to be particularly suitable for providing axial and lateral stability but, for the most part, have not been retrievable or aesthetically acceptable.

On the other hand, indexing elements with faceted surfaces have commonly been employed in artificial teeth and the like having a single anchor point or implant. In these applications, the faceted surfaces, typically a hexagonal configuration, have been found to be particularly suitable for providing angular or rotational stability.

The above discussion of particularly configured indexing elements is only representative of the prior art. However, it is particularly noted that the prior art has employed either tapered or faceted indexing elements. In addition, the prior art has employed faceted surfaces which are also tapered. See U.S. Pat. No. 4,016,651 issued Apr. 12, 1977 to Kawahara et al and U.S. Pat. No. 3,905,109 issued Sep. 16, 1975 to Cohen et al.

The use of such a variety of implants naturally led to a wide assortment of parts available for use by practitioners such as dentists. At the same time, such appliance mountings were sometimes limited in application by not being able to provide a desired combination of features such as axial and lateral stability, as well as angular or rotational stability in addition to patient comfort, esthetics and maintenance.

SUMMARY OF THE INVENTION

Accordingly, there has been found to remain a need for an improved universal modification abutment for securing appliances in place upon implants in bony substrates. More particularly, there has been found to remain a need for such abutments which are capable of providing both axial and lateral stability as well as angular rotational stability for a two-fold purpose. Initially, such abutments are capable of substantially reducing the number of different parts available for specific applications and provide even further enhanced stability for the appliances as well as esthetics, patient comfort and maintenance. Furthermore, if desired by the patient, the same universal modification abutment may be used with one application (such as an overlay denture) and later with another application (such as a bridge).

Accordingly, it is a further object of the invention to provide an abutment for dental or physiological appliances in order to overcome one or more problems of the type summarized above.

More specifically, it is an object of the invention to provide an abutment for securing dental or other physiological appliances to an implant in a bony substrate, the abutment including means forming an abutment surface facing outwardly from the implant and an indexing element having a cylindrical tapered surface extending outwardly (normally vertically) from the abutment surface and one or more planar facets intersection the tapered surface adjacent the abutment surface, the planar facets being arranged on the indexing element so that intermediate portions of the tapered surface extend substantially to the abutment surface.

It is important to note that the planar facets are parallel to a longitudinal axis of the abutment, as illustrated in FIGS. 5, 6, 9, et al. The purpose of the planar facets being parallel to the longitudinal axis of the abutment is to adapt them for accurate alignment and engagement with similarly configured portions of tools and/or appliances.

Such an abutment offers wide versatility since it can be employed with appliances including either a tapered surface, faceted surfaces or a combined tapered/faceted surfaces. Faceted surfaces on the indexing element provide optimum angular or rotational stability while the tapered surface provides optimum axial or lateral stability. With the appliance including both a mating tapered surface and mating faceted surfaces with separate attachment means discussed below, both types of stability are achieved in a single mounting.

Further versatility is achieved since the abutment of the present invention may be employed either for appliances such as artificial teeth having a single anchor point or implant as well as appliances such as dentures and the like normally including two or more anchor points or implants.

The abutment is preferably formed with multiple faceted surfaces, preferably from three to twelve such surfaces, more preferably three to eight such surfaces and most preferably six such surfaces in a hexagonal configuration to facilitate formation of the appliance for mating with the indexing element. The number of faceted surfaces or planar facets must be maintained within the above ranges in order to assure proper engagement with various tools and implements. The number of planar facets is limited in order to prevent the planar surfaces from being stripped on either the abutment or the mating tool or implement during installation or removal, for example.

The abutment may be formed according to the present invention with the indexing element either being an integral portion of the implant, the abutment surface then being formed on an outer end of the implant, or with a separate insert forming both the abutment surface and the indexing element, the insert then further including means for attachment to the implant.

It is another object of the invention to provide an abutment as described above together with separate attachment means for securing an appliance or the like to the abutment. In contrast to prior art configurations where the appliance is cemented or permanently affixed to the abutment, this feature of the invention permits "retrievable restoration" of the appliance. The separate attachment preferably comprises a threaded socket centrally formed on the indexing element of the abutment for threaded engagement with the appliance. With the abutment also being threaded or removably attached to the implant, the abutment is thus also capable of retrievable restoration in order to facilitate maintenance or modification of the implement, abutment, etc.

Preferably, the tapered surface forms an angle generally within the range of about ten to thirty degrees relative to an axis of the indexing element, more preferably an angle within the range of about thirteen to seventeen degrees. Such an angle has been found to be generally desirable for enhancing stability of the abutment for the appliance. Preferred dimensions are also set forth below for the mount. However, it is generally contemplated by the invention to provide a variety of configurations for the abutment with certain features including the diameter of the abutment surface, the configuration of the tapered surface and the planar surfaces being uniform so that all of the various configurations mate with the same abutment devices in the appliance. At the same time, it is generally desirable to maintain relatively minimum dimensions for the abutment, particularly the indexing element in order to permit proper design of the appliance.

The combination of the cylindrically tapered surface on the indexing element, the multiple planar facets parallel to the axis of the mount abutment and the separate attachment means for removably securing the appliance to the abutment are essential in combination to make the abutment of the present invention a "universal modification abutment" suitable for single teeth, bridges or overdentures (that is, a denture releasably attached to posts or the like). The above combination of features also permits and facilitates maintenance since the abutment is removable from a supporting implant as well as the appliance. Further in connection with the above combination, it is also important that both the tapered surface and the planar facets extend substantially toward a surrounding abutment surface for assuring proper engagement of an appliance or tool with the tapered surface and/or the multiple faceted surfaces.

Additional objects and advantages of the invention are made apparent in the following description having reference to the accompanying drawings.

BRIEF DESCRIPTION OF THE DRAWINGS

FIG. 7 is a pictorial view of an implant with abutment features of the present invention integrally formed thereupon.

FIGS. 8 and 9 are respectively a side view and top view of the implant of FIG. 7.

FIG. 10 is a fragmentary, partially sectioned view of an abutment from the artificial tooth of FIG. 2 and having an internal socket mating with the indexing element of the invention.

FIG. 11 is an end view of the abutment of FIG. 10 to further illustrate the socket configuration.

DESCRIPTION OF THE PREFERRED EMBODIMENTS

As noted above, the present invention relates to an abutment device or assembly and a method of use for the abutment to secure physiological or dental appliances to an implant embedded within a bony substrate of the body. For dental appliances, the bony substrate is provided by the jawbone normally supporting the teeth. As is well known to those skilled in the art, such appliances are normally secured to the bony substrate by one or more anchor points or implants directly or indirectly, depending upon the configuration of the appliance as discussed above.

The invention generally contemplates a variety of maxiofacial restoration appliances and more particularly appliances for dental applications including artificial teeth, dentures, bridges, overlay dentures with bars, stud attachments, etc., interconnected to artificial teeth or a combination of artificial and natural teeth. Such appliances may also include variations of those summarized above such as telescopic units and misalignment units suitable for use with or to replace misangled teeth for example.

Figure 3:
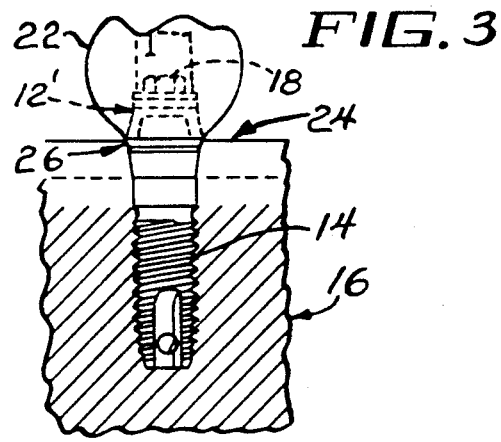
FIG. 3 is an enlarged longitudinally sectioned view similar to FIG. 2 to better illustrate construction of an abutment according to the invention.

Generally, abutment features of the present invention may be provided either by a separate abutment as indicated at 26 for the abutment 24 of FIG. 3 or integrally with an implant such as that indicated at 114 in FIG. 7. Those embodiments of the invention are described in greater detail below.

Figure 1:
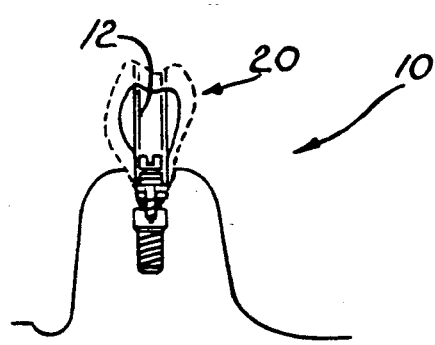
FIGS. 1 and 2 represent conventional steps in employing a mounting device to mold a dental appliance such as a fixed removable artificial tooth illustrated in FIG. 2, the artificial tooth also including a similarly configured mounting secured for example by means of a screw to an abutment assembly positioned on an implant and constructed according to the present invention.
Figure 2:
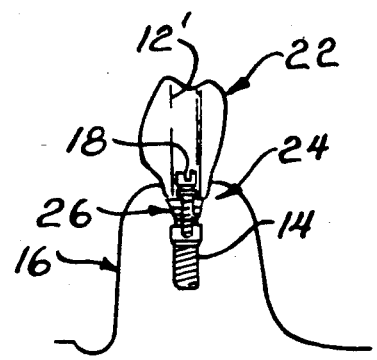

Referring initially to FIGS. 1 and 2, a dental appliance of the type contemplated by the present invention may be in the form of a casting assembly 10 wherein a plastic or elastomeric abutment device 12 is attached to an implant 14 embedded within the bony substrate or jawbone 16 by means of a screw 18 in order to provide a base for forming a model 20 of an appliance or artificial tooth indicated at 22 in FIG. 2.

As noted above, the method of forming artificial teeth or other dental appliances is well known to those skilled in the art and is accordingly not described in greater detail herein. For purposes of the present inventions, it is sufficient to understand that during preparation or formation of the artificial tooth 22 of FIG. 2, the plastic component 12 of FIG. 1 is replaced by a hard metal device 12' within the artificial tooth 22 of FIG. 2.

Furthermore, the artificial tooth 22 is also representative of a wide variety of appliances contemplated by the present invention and described in greater detail above. Generally all such appliances are mounted by means or one or more anchor points or implants such as that indicated at 14.

As noted above, the present invention particularly contemplates generally indicated at 24 for securing either the casting assembly 10 of FIG. 1 or the artificial tooth of FIG. 2 or any of a variety of other appliances to the bony substrate. More particularly, the assembly 24 provides a means for securing the device 12 of 12' of FIGS. 1 and 2 respectively to the implant 14. Performance of the abutment 24 is particularly important in connection with the artificial tooth or finished appliance 22 of FIG. 2 because of substantial forces which can be applied either radially or laterally as well as angularly or rotationally to the tooth in its normal use.

Figure 4:
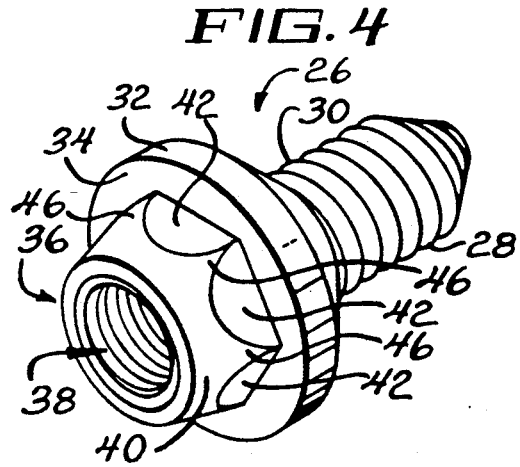
FIG. 4 is a pictorial view of an abutment adapted to be threaded into the implant and having both the abutment surface and indexing element formed thereon.
Figure 6:
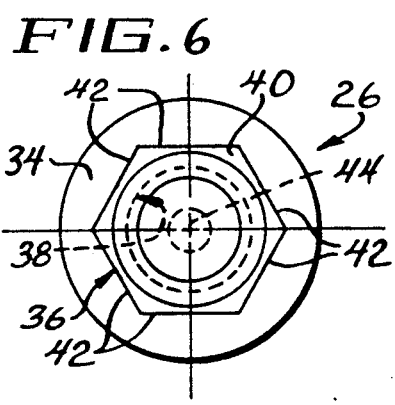
FIG. 6 is a top view of the abutment of FIG. 4.
Figure 5:
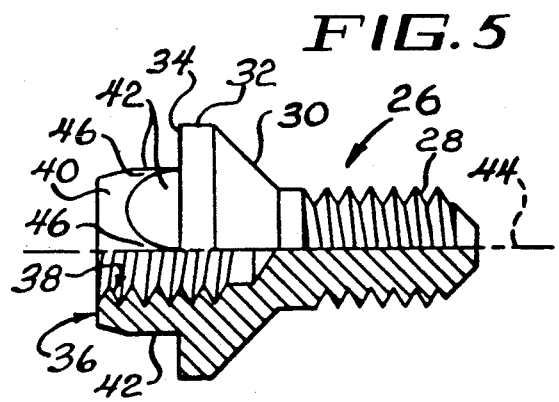
FIG. 5 is a partially sectioned side view of the abutment of FIG. 4.

The present invention contemplates formation of the assembly or device 24 either as a separate part 26 illustrated in FIGS. 4-6 and attachable to the implant 14 or integrally with the implant 114 as illustrated in FIGS. 7-9. Those embodiments of the invention are described in greater detail below.

The abutment 26 in the assembly 24 of FIGS. 1 and 2 is illustrated in greater detail in FIGS. 4-6. Referring to those figures, the separate abutment 26 is threaded at its inner end 28 adjacent a tapered shoulder 30. As illustrated in FIGS. 1 and 2, the threads 28 and tapered shoulder 30 mate with corresponding portions of the implant in order to firmly secure the abutment 26 in place upon the implant. The abutment 26 could also be provided with other means for removably attaching the abutment to the implant, for example by means of press-fit engagement, such as with a Jacob's taper. It would of course also be possible to cement or otherwise permanently fix the abutment 26 to the implant 14 of FIGS. 1 and 2.

Outwardly from the tapered shoulder 30, the abutment 26 is provided with a cylindrical extension 32 forming an abutment surface 34 and abutment an indexing element 36. The indexing element 36 is centered upon the abutment surface 34 and is formed with a threaded socket 38 for receiving the screw 18 (see FIGS. 3 and 4) for securing the abutment device 12 and the casting assembly 10 in place. The socket 38 also provides a separate attachment means for removably securing the appliance or tooth 22 in place upon the abutment 26. The socket 38 or attachment means for the appliance thus cooperates with the abutment surface 34 as well as the tapered surface 40 and faceted surfaces 42, described below, to assure that the appliance is secured in proper engagement with those surfaces.

The indexing element 36 forms a cylindrically tapered surface 40 extending substantially from the abutment surface 34 axially outwardly on the indexing element. Preferably, the tapered surface 40 extends along the entire axial length of the indexing element 36. Accordingly, the tapered surface 40 may be seen in FIGS. 4-6 to have a frustoconical configuration.

One or more faceted surfaces 42 are superimposed upon or cut into the tapered surface 40 adjacent the abutment surface 34. The faceted surfaces 42 are preferably formed parallel with the axis 44 of the indexing element 36 and are relatively arranged upon the indexing element so that at least portions of the tapered surface 40 continue to extend substantially into engagement with the abutment surface 34.

Preferably, multiple faceted surfaces 42 are formed upon the indexing element 36 in at least slightly spaced apart relation so that portions of the tapered surface 40 intermediate each adjacent pair of faceted surfaces 42 extend substantially into engagement with the abutment surface 34. Referring particularly to FIG. 4, the invention preferably contemplates from three to twelve, more preferably from three to eight and most preferably six faceted surfaces 42 formed in a hexagonal configuration with six intermediate portions 46 of the tapered surface extending substantially into engagement with the abutment surface 34. The tapered surface 40 thus has substantial six-point engagement with the appliance or device 12, 12' of FIGS. 1 and 2 respectively adjacent the abutment surface 34.

Because of the configuration of the indexing element 36, the abutment 26 is suitable for rigidly supporting an abutment device having a socket with either a tapered surface and/or faceted surface configuration. Such configurations are discussed further below with reference to FIGS. 10 and 11.

In order to made the abutment 26 even more versatile, different configurations of the abutment are preferably made available with cylindrical extensions 32 of different axial lengths or heights. Thus, a dentist or other user is able to select from a series or abutments in order to better fix a particular application. At the same time, the abutments 26 are preferably formed with uniform dimensions for the diameter of the abutment surface 34, the angular configuration and length of the tapered surface 40 and the configuration of the faceted surfaces 42 so that all of the abutments uniformly mate with the same abutment devices.

Referring again to the abutment 26 of FIGS. 4-6, its dimensions are set forth below, not for the purpose of specifically limiting the invention, but to better emphasize its function. For example, the overall height or axial length of the indexing element 36 is preferably at least about 0.020 inches, more preferably within the range of about 0.030-0.100 inches and most preferably about 0.050 inches. At the same time, the faceted surfaces 42 extend outwardly from the abutment surface 34 at least about one-half the axial length of the tapered surface 40 and the overall length of the indexing element 36.

The tapered surface 40 is preferably angled within the range of about ten to thirty degrees relative to the axis 44 of the indexing element. More preferably, the angle of the surface 40 is within the range of about thirteen to seventeen degrees.

These dimensions and configurations have been found generally preferable in order to permit design flexibility and use for a variety of appliances. At the same time, the dimensions and particularly the angular configuration of the surface 40 is selected to achieve optimum stability for the appliance.

The abutment 26, being formed separately from the implant, is preferably formed from a hard metal such as titanium which is commonly employed in such applications. The abutment could also be formed from other suitable metals such as gold or possibly other alloys. However, titanium is presently employed in practically all such devices. It is also noted that the abutment could be formed from an acetal resin such as that available under the trade name DELRIN. That material has similar properties as periodontal ligaments and is thus suitable for use in such applications.

As noted above, abutment components including the indexing element 36 and abutment surface 34 may also be integrally formed with the implant 14. Such an implant is illustrated at 114 in FIGS. 7-9. An abutment surface 134 is formed on an outer end of the implant 114 with an indexing element 136 being integrally formed upon the implant 114 in centered relation upon the abutment surface 134. Otherwise, the abutment surface 134 and indexing element 136 have substantially similar features as the abutment surface 34 and the indexing element 36 of FIGS. 4-6. Corresponding features to those elements are indicated by similar numerical labels as in FIGS. 4-6 but with the additional preceding digit "1".

The implant 114 is also adapted for being conventionally secured in place within a bony substrate such as indicated at 16 in FIGS. 1 and 2. For example, the barrel 152 of the implant 114 is preferably threaded for replaceably securing the implant in place. Here again, the implant could be provided with other attachment means such as press-fit engagement or merely being cemented in place as noted above.

The preferred dimensions and configurations for the abutment surface 134 and indexing element 136 are similar to those described above for the abutment surface 34 and the indexing element 36 of FIGS. 4-6.

With those components being integrally formed by the implant, the implant is preferably formed again from a metal, most preferably titanium. However, other materials known to those skilled in the art may also be employed for forming the implant. Such materials include crystal sapphire, alumina and titanium coated with hydroxyl apatite.

As noted above, the appliance employed in combination with the abutment of the present invention may have either a tapered configuration, a faceted configuration or a combination tapered/faceted configuration adapted to mate with the exterior of the indexing element 36 of FIGS. 4-6 or the indexing element 135 of FIGS. 7-9. Regardless of the configuration selected, it is of course important that the configuration closely mate with the corresponding portions of the indexing element. At the same time, the appliance includes a surface configured for abutting and substantially mating with the abutment surface 34 or 134.

A novel configuration for an abutment constructed according to the present invention is illustrated in FIGS. 10 and 11. Referring to those figures, an enlarged device corresponding to that indicated at 12' in FIG. 2 is illustrated. The device 12' is formed with a socket 154. The configuration of the socket 154 includes both a tapered surface 156 mating with the tapered surface 40 or 140 of the two embodiment described above. At the same time, the socket 154 is also formed with facets 158 arranged to mate closely with the faceted surfaces 42 ore 142 of the two embodiments described above. Such a configuration for the socket of the device 12' is believed to provide even greater stability for the appliance and compared to an abutment device with only a tapered surface or faceted surfaces.

Preferably, both the faceted surfaces 158 of the socket 154 for the device 12' and the faceted surfaces of an indexing element are formed with a plurality of six surfaces arranged in a hexagonal configuration in order to facilitate the manufacture of both components.

Accordingly, there has been described above multiple embodiments of an effective abutment for dental or physiological appliances. A method of use for the abutment or abutments has also been provided above together with structural features of the abutment.

Numerous modifications will be apparent in addition to those specifically noted above. Accordingly, the scope of the present invention is defined only by the following claims which are also set forth as further examplary of the invention.

What is claimed is:

1. An abutment for securing dental appliances such as artificial teeth or dentures to an implant anchored in a bony substrate, comprising
   means forming an abutment surface positioned for facing outwardly from the bony substrate, and
   an indexing element centrally arranged on the abutment surface, the indexing element forming
   (a) a cylindrical tapered surface extending outwardly from the abutment surface, (b) a plurality of planar facets each parallel with a longitudinal axis of the abutment and intersecting the tapered surface adjacent the abutment surface, the planar facets further being arranged on the indexing element with intermediate portions of the tapered surface extending substantially toward the abutment surface, and (c) an axially positioned threaded element for replacing an appliance on the abutment.

2. The abutment of claim 1 adapted for use with dental appliances comprising a device having a surface for engaging the abutment surface and a socket for receiving the indexing element, the socket having an interior configuration selected from the class consisting of a tapered surface, faceted surfaces and combined tapered/faceted surfaces, the indexing element being configured for mating with any of the class.

3. The abutment of claim 1 being formed in a variety of configurations with uniform dimensions of the tapered surface and the faceted surfaces for mating engagement with a variety of dental appliances.

4. The abutment of claim 1 wherein the indexing element forms three to twelve faceted surfaces.

5. The abutment of claim 1 wherein the indexing element forms three to eight faceted surfaces.

6. The abutment of claim 1 wherein the indexing element is formed with six multiple planar facets in a hexagonal configuration, the tapered surface extending substantially to the abutment surface at six locations intermediate respective adjacent pairs of facets.

7. The abutment of claim 6 wherein the dental appliance comprises a device having a surface for engaging the abutment surface and a socket for receiving the indexing element, the socket having an interior configuration closely mating with the tapered surface and the six planar facets when the appliance is threaded securely onto the abutment.

8. The abutment of claim 1 formed as an integral part of the implant.

9. The abutment of claim 1 further comprising threaded means for removable engagement with the implant whereby both the appliance and abutment are capable of retrievable restoration.

10. The abutment of claim 9 being formed in a variety of configurations with uniform dimensions of the tapered surface and the faceted surfaces and further comprising an extension of various heights between the implant and the abutment surface.

11. The abutment of claim 8 being formed in a variety of configurations with uniform dimensions of the tapered surface and the faceted surfaces and further comprising an extension of various heights between the implant and the abutment surface.

12. The abutment of claim 1 wherein the tapered surface extends substantially from the abutment surface to an outer end of the indexing element, the taper being in the range of about ten to thirty degrees relative to an axis of the indexing element.

13. The abutment of claim 12 wherein the taper is in the range of about thirteen to seventeen degrees.

14. The abutment of claim 12 wherein the facets extend at least about one-half the axial length of the tapered surface.

15. The abutment of claim 12 wherein the overall axial length of the indexing element is at least about 0.020 inches.

16. The abutment of claim 15 wherein the overall axial length of the indexing element is in the range of about 0.030–0.100 inches.

17. A abutment for securing physiological appliances to an implant anchored in a bony substrate, comprising
means forming an abutment surface positioned for facing outwardly from the bony substrate, and
an indexing element centrally arranged on the abutment surface, the indexing element forming
(a) cylindrical tapered surface extending outwardly from the abutment surface,
(b) a plurality of planar facets each parallel with a longitudinal axis of the abutment and intersecting the tapered surface adjacent the abutment surface, the planar facets further being arranged on the indexing element with intermediate portions of the tapered surface extending substantially toward the abutment surface, and
(c) an axially positioned threaded element for replacing an appliance on the abutment.

18. The abutment of claim 17 adapted for use with physiological appliances comprising a device having a surface for engaging the abutment surface and a socket for receiving the indexing element, the socket having an interior configuration selected from the class consisting of a tapered surface, faceted surfaces and combined tapered/faceted surfaces, the indexing element being configured for mating with any of the class.

19. The abutment of claim 18 being formed in a variety of configurations with uniform dimensions of the tapered surface and the faceted surfaces for mating engagement with a variety of dental appliances.

20. The abutment of claim 17 wherein the indexing element is formed with three to twelve planar facets.

21. The abutment of claim 17 wherein the indexing element is formed with three to eight planar facets.

22. The abutment of claim 17 wherein the tapered surface extends substantially from the abutment surface to an outer end of the indexing element, the taper being in the range of about ten to thirty degrees relative to an axis of the indexing element.

23. The abutment of claim 22 wherein the facets extend at least about one-half the axial length of the tapered surface.

24. The abutment of claim 17 being formed as an integral part of the implant.

25. The abutment of claim 17 further comprising threaded means for removable engagement with the implant whereby both the appliance and abutment are capable of retrievable restoration.

* * * * *